(12) United States Patent
Wilson et al.

(10) Patent No.: US 9,927,346 B2
(45) Date of Patent: Mar. 27, 2018

(54) FLOW CYTOMETER SYSTEM INCLUDING FLOW CYTOMETER, AUTOSAMPLER AND SYSTEM INTEGRATION STRUCTURE

(71) Applicant: IntelliCyt Corporation, Albuquerque, NM (US)

(72) Inventors: Garrett S. Wilson, Erie, CO (US); Braden L. Smith, Lafayette, CO (US); Michael A. Artinger, Boulder, CO (US); Francis Kevin Kohlmeier, Tigard, OR (US); Christopher H. Converse, Boulder, CO (US)

(73) Assignee: IntelliCyt Corporation, Albuquerque, NM (US)

( * ) Notice: Subject to any disclaimer, the term of this patent is extended or adjusted under 35 U.S.C. 154(b) by 0 days.

(21) Appl. No.: 15/715,464

(22) Filed: Sep. 26, 2017

(65) Prior Publication Data

US 2018/0017479 A1    Jan. 18, 2018

Related U.S. Application Data

(62) Division of application No. 15/127,732, filed as application No. PCT/US2015/020512 on Mar. 13, 2015.

(60) Provisional application No. 61/969,021, filed on Mar. 21, 2014.

(51) Int. Cl.
| | | |
|---|---|---|
| *B01L 9/00* | (2006.01) | |
| *G01N 33/00* | (2006.01) | |
| *C12Q 1/68* | (2006.01) | |
| *G01N 15/14* | (2006.01) | |
| *G01N 35/10* | (2006.01) | |
| *B01L 3/00* | (2006.01) | |

(52) U.S. Cl.
CPC .......... *G01N 15/1404* (2013.01); *B01L 3/502* (2013.01); *G01N 15/1459* (2013.01); *G01N 35/1095* (2013.01); *B01L 2200/026* (2013.01); *B01L 2300/0609* (2013.01); *B01L 2300/0858* (2013.01); *B01L 2300/0867* (2013.01); *B01L 2300/123* (2013.01); *G01N 2015/1409* (2013.01)

(58) Field of Classification Search
USPC ....... 422/73, 50, 401, 565, 566, 311; 436/10
See application file for complete search history.

(56) References Cited

U.S. PATENT DOCUMENTS

| | | | |
|---|---|---|---|
| 5,229,074 A | 7/1993 | Heath et al. | |
| 5,934,885 A * | 8/1999 | Farrell | F04B 43/06 417/250 |
| 6,592,822 B1 * | 7/2003 | Chandler | G01N 15/1456 356/72 |
| 7,198,956 B2 | 4/2007 | Uffenheimer et al. | |
| 7,758,811 B2 | 7/2010 | Durack et al. | |
| 2005/0123445 A1 | 6/2005 | Blecka et al. | |
| 2015/0192573 A1 | 7/2015 | Fukuma et al. | |

* cited by examiner

*Primary Examiner* — Dean Kwak
(74) *Attorney, Agent, or Firm* — Marsh Fischmann & Breyfogle LLP

(57) ABSTRACT

A flow cytometer system includes a flow cytometer, an autosampler and a system integration structure to accommodate interconnection and interface of the flow cytometer and autosampler for operation together and providing for convenient interface with equipment for handling process liquids.

2 Claims, 7 Drawing Sheets

FLOW CYTOMETER SYSTEM INCLUDING FLOW CYTOMETER, AUTOSAMPLER AND SYSTEM INTEGRATION STRUCTURE

CROSS-REFERENCE TO RELATED APPLICATIONS

This application is a divisional of U.S. patent application Ser. No. 15/127,732 entitled "FLOW CYTOMETER SYSTEM INCLUDING FLOW CYTOMETER, AUTOSAMPLER AND SYSTEM INTEGRATION STRUCTURE" having a 371(c) date of Sep. 20, 2016, which is a U.S. national stage filing under the Patent Cooperation Treaty of international patent application no. PCT/US2015/020512 filed Mar. 13, 2015, which claims the benefit of U.S. provisional patent application No. 61/969,021 entitled "FLOW CYTOMETER SYSTEM INCLUDING FLOW CYTOMETER, AUTOSAMPLER AND SYSTEM INTEGRATION STRUCTURE" filed Mar. 21, 2014, the entire contents of each of which are incorporated herein by reference.

FIELD OF THE INVENTION

The invention relates to flow cytometry, including in relation to equipment and systems.

BACKGROUND OF THE INVENTION

Flow cytometry is an analytical technique used in a number of applications to measure physical and/or chemical properties of biological or nonbiological particles as they flow in a sample fluid, often an aqueous liquid medium, through an investigation cell. Flow through the cell may be investigated by a variety of techniques, including subjecting the flow to electrical, acoustic and/or optical signals in measuring and analyzing responses to detect and evaluate particles in the sample.

In order to increase the number of samples that may be processed, a flow cytometer may be coupled to process sample fluids provided by an autosampler. A number of flow cytometer manufacturers have specially designed autosamplers that connect and interface with their flow cytometer product. Such coordinated design between the flow cytometer and autosampler provides convenience to the user, but may limit the combinations of different autosamplers and flow cytometers that may be used in combination. Furthermore, some flow cytometers may not be provided by a manufacturer that also provides an autosampler with a coordinated design, which may limit the utility of the flow cytometers to processing only manually provided sample fluid batches.

Although it may be possible in some circumstances to adapt an autosampler and flow cytometer that do not have a coordinated design to operate together, such adaptation may often be difficult to achieve and my result in poor interconnection of system components and/or poor space utilization.

SUMMARY OF THE INVENTION

In one aspect, a flow cytometer system is disclosed that includes a flow cytometer, an autosampler and a system integration structure that may provide operational interface between the autosampler and the flow cytometer and process liquid containers that may provide process liquids to or receive process liquids from the flow cytometer and the autosampler. The flow cytometer has a sample inlet for receiving a sample fluid for flow cytometry analysis of the sample fluid for particles within the sample fluid. The autosampler is in fluid communication with the sample inlet of the flow cytometer, and the autosampler may be operative to automatically provide a series of batches of sample fluid to the flow cytometer for flow cytometry analysis. The system integration structure includes an upper shelf disposed above the autosampler and on which the flow cytometer is supported above the autosampler. The system integration structure includes a container rack that has a plurality of receptacles to receive a corresponding plurality of process liquid containers.

In another aspect, a system integration structure, or unit, is disclosed, such as may be used in the flow cytometer system of the above-noted aspect. For example, the system integration structure may be, or may include any feature or features of, the system integration structure of the flow cytometer system.

A number of feature refinements and additional features may be applicable to the flow cytometer system aspect and/or the system integration structure aspect of this disclosure, as further disclosed below in the detailed description and with reference to the drawings and/or as disclosed in the claims presented below. These feature refinements and additional features may be used individually or in any combination. As such, each such feature may be, but is not required to be, used with any other feature or combination with any one or more features of the flow cytometer system aspect and/or the system integration structure aspect.

DETAILED DESCRIPTION

Figure 1:
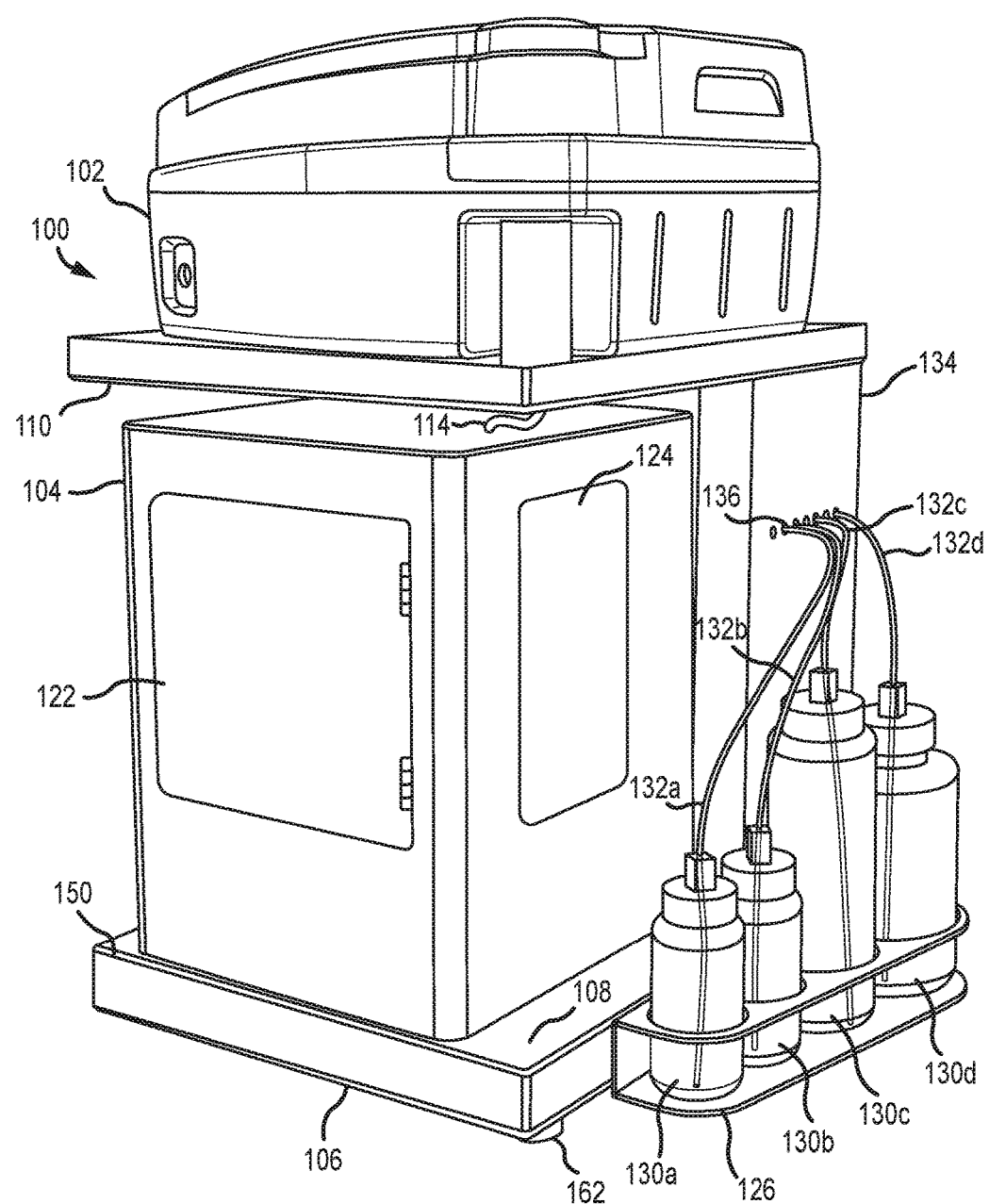
FIG. 1 illustrates an embodiment of a flow cytometer system.
Figure 2:
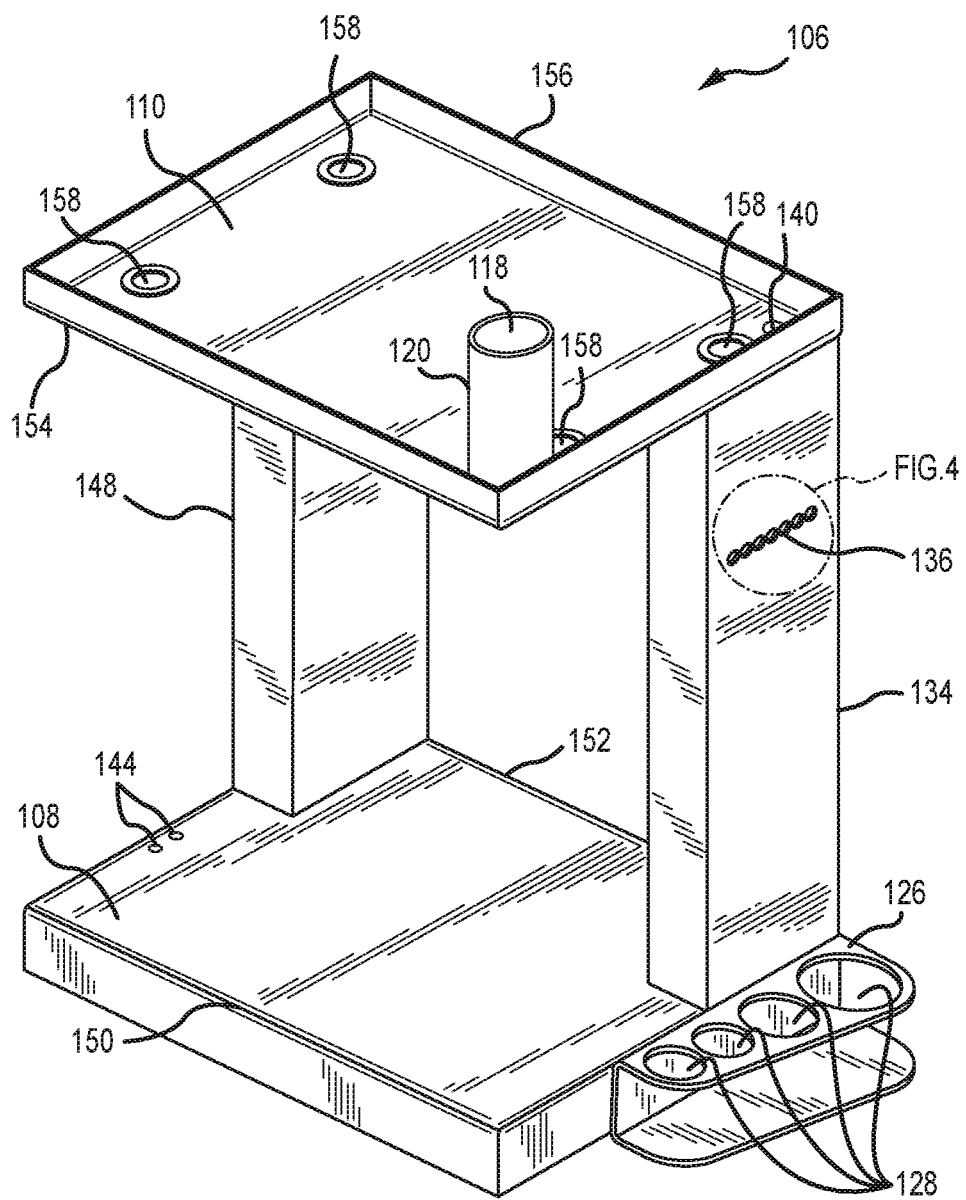
FIG. 2 is a perspective view of a system integration structure shown in the flow cytometer system embodiment of FIG. 1.
Figure 3:
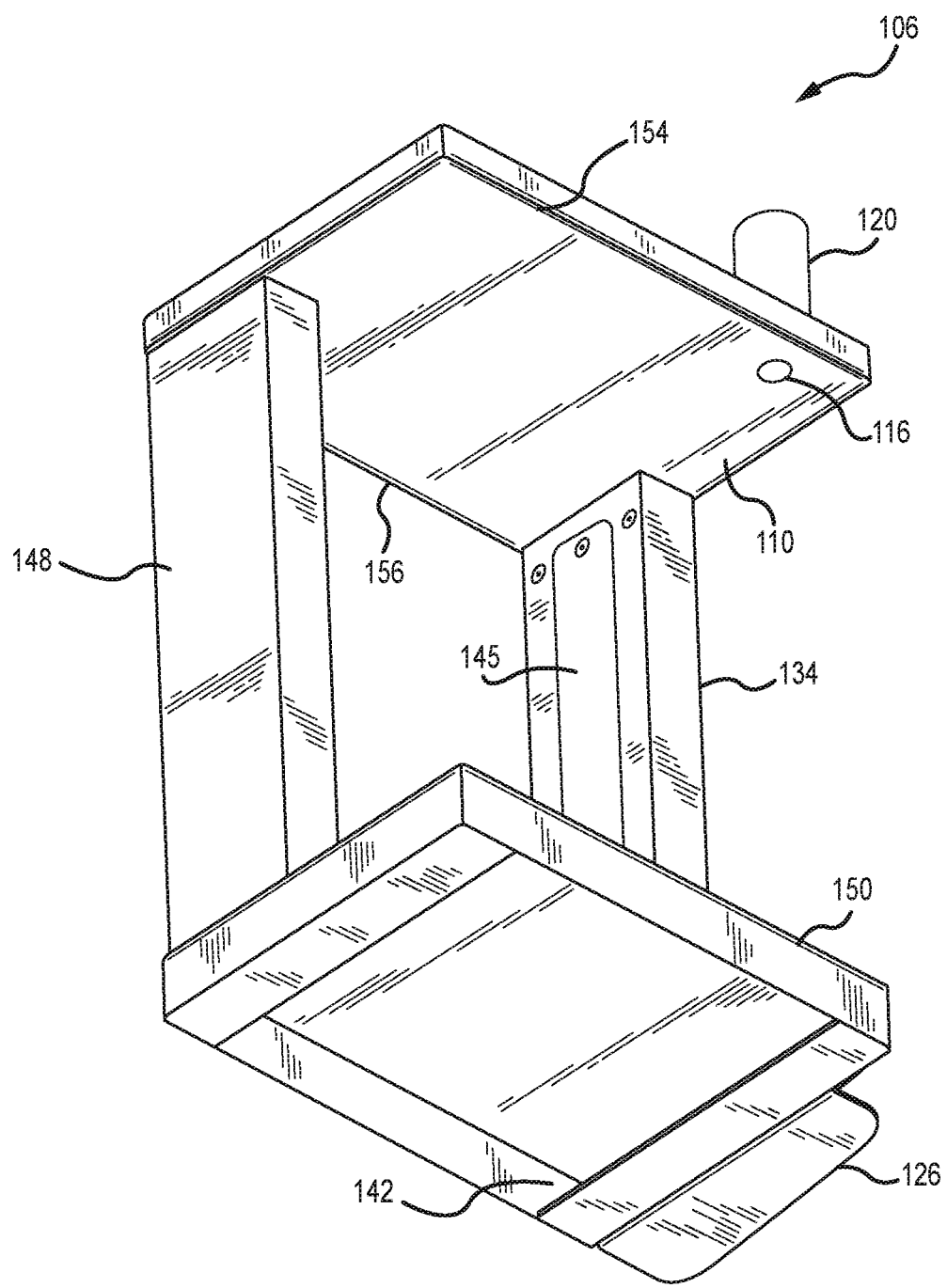
FIG. 3 is another perspective view of the system integration structure shown in FIG. 2.
Figure 4:
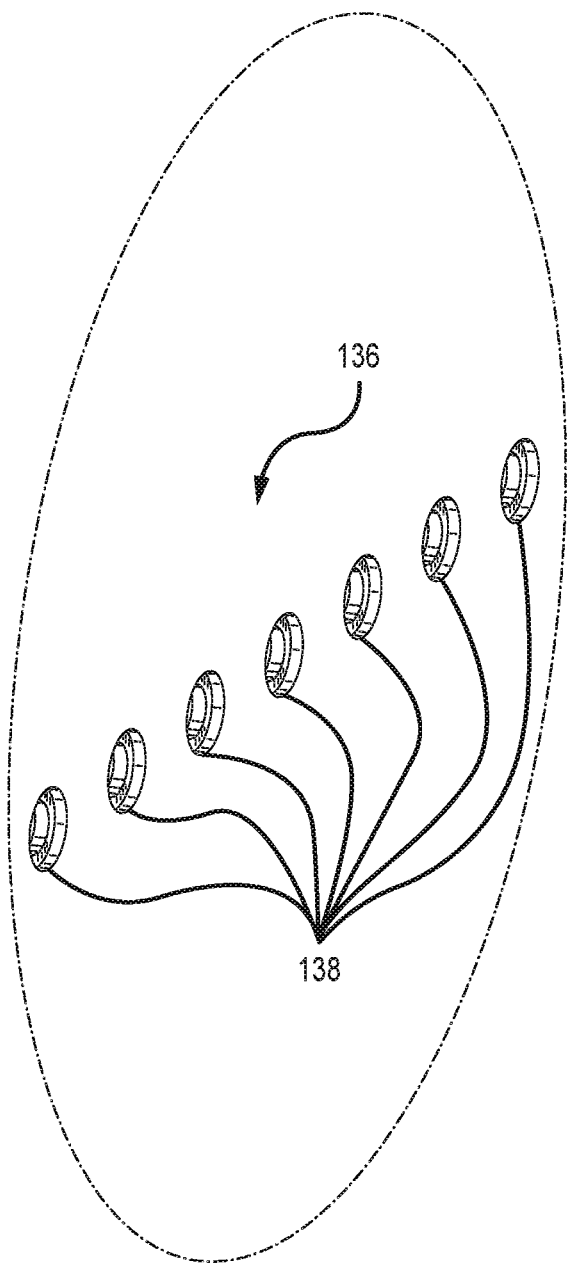
FIG. 4 is an enlarged view of a portion of the system integration structure shown in FIG. 2.
Figure 5:
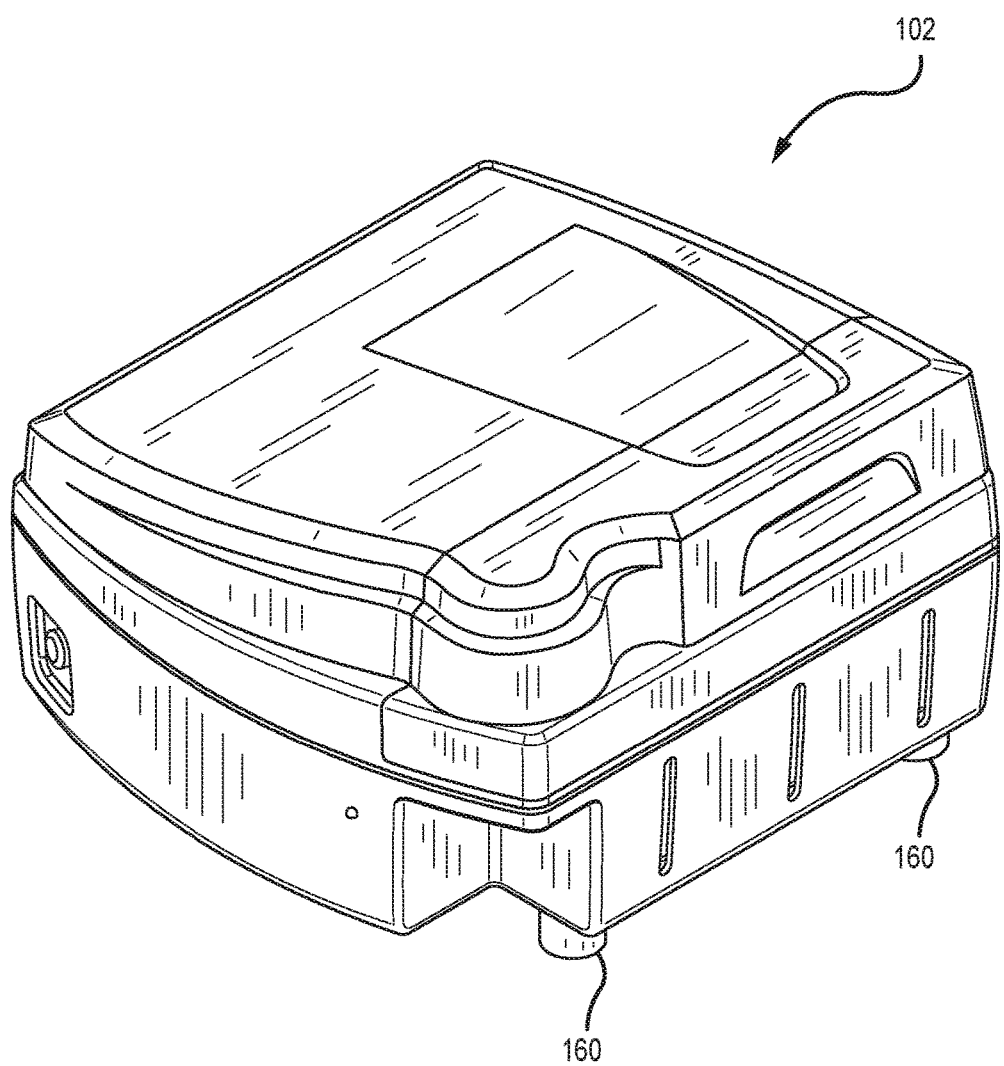
FIG. 5 is a perspective view of the flow cytometer shown in the flow cytometer system embodiment of FIG. 1.
Figure 6:
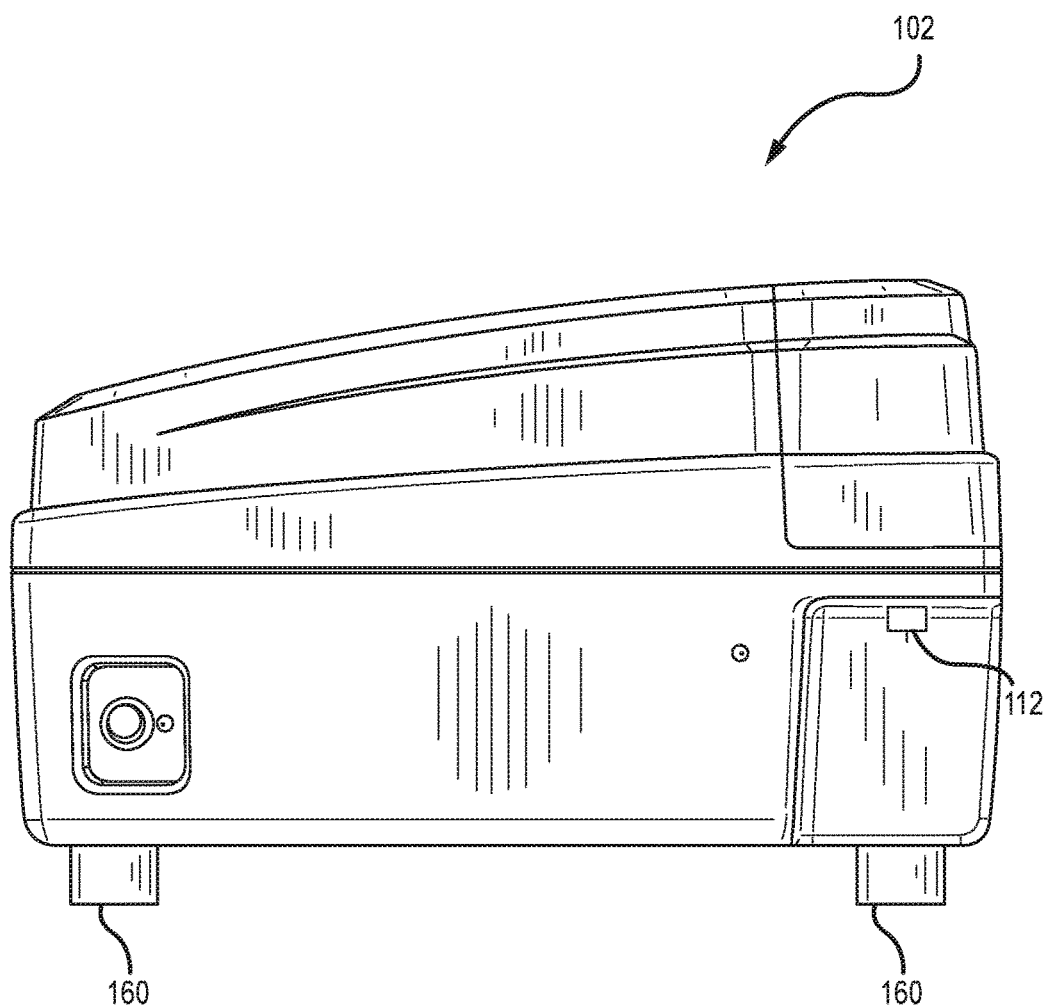
FIG. 6 is a front view of the flow cytometer shown in FIG. 5.
Figure 7:
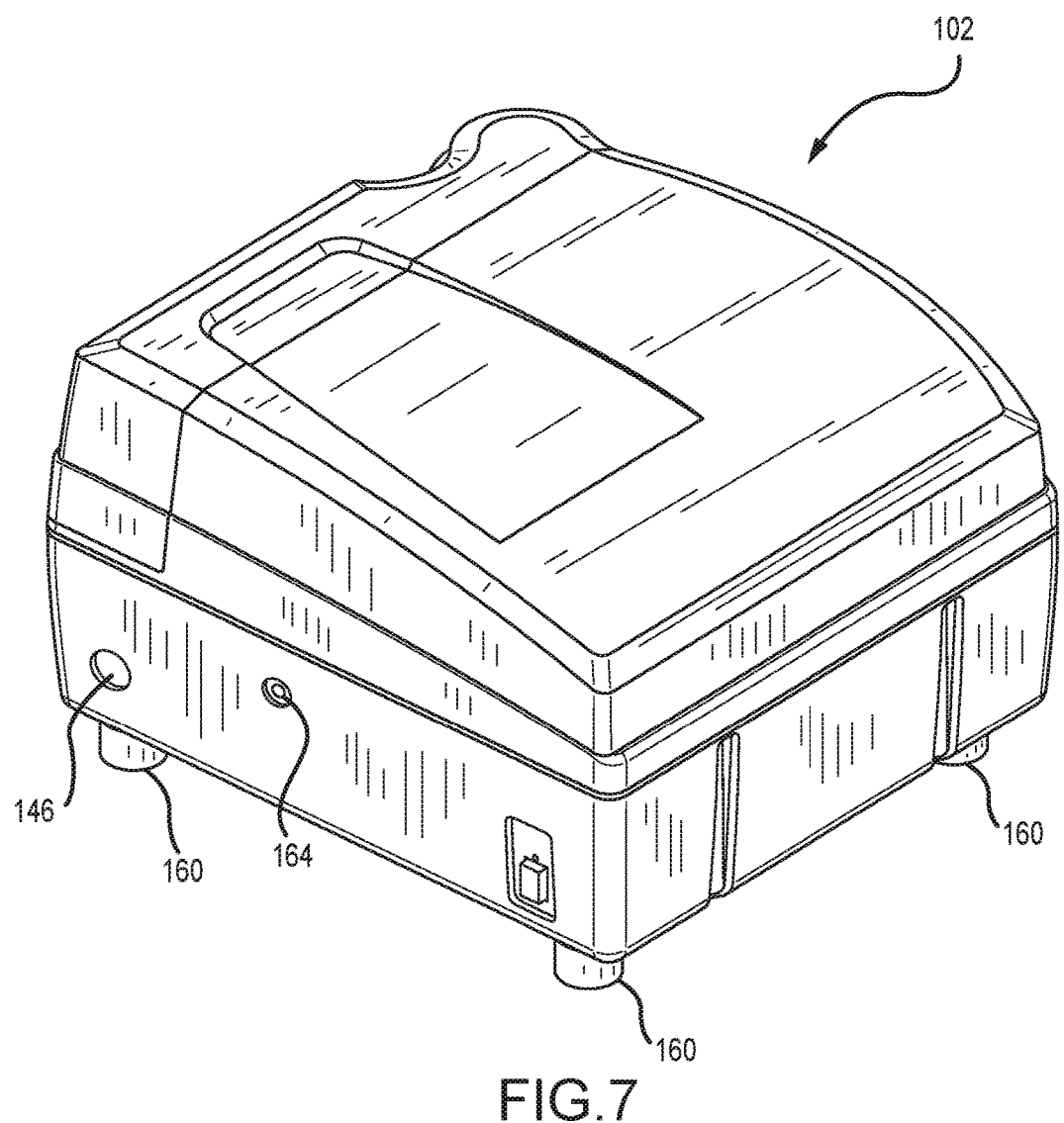
FIG. 7 is another perspective view of the flow cytometer shown in FIG. 5.

FIG. 1 shows an example implementation of a flow cytometer system 100 including a flow cytometer 102, an autosampler 104 and a system integration structure 106. More detail on the system integration structure 106 is shown in FIGS. 2-4 and more detail on the flow cytometer 102 is shown in FIGS. 5-7. The flow cytometer system 100 and components thereof will now be described with reference to FIGS. 1-7.

The system integration structure 106 includes a lower shelf 108, on which is supported the autosampler 104, and an upper shelf 110, on which is supported the flow cytometer 102. The flow cytometer 102 has a sample inlet 112 (shown in FIG. 6) that is in fluid communication with the autosampler 104 to receive batches of sample fluid for flow cytometry analysis in the flow cytometer 102 through a sample feed conduit 114. The sample feed conduit 114 passes through a passage 116 through the upper shelf 110 into an internal passage 118 of a riser 120 of the system integration structure 106. The sample inlet 112 is disposed in the internal passage 118 of the riser 120 to be protected by the wall of the riser 120. During operation, the autosampler 104 may automatically sample batches of sample fluid to be analyzed, such as may be provided in a multi-well sample tray that may be disposed in the autosampler 104 through the front access provided by a front door 122 of the autosampler 104. The autosampler 104 may also have a side access 124, which as shown in FIG. 1 may be in the form of an access panel that may be removable to provide access through the side of the autosampler 104, such as for maintenance purposes or to replace reagent bottles that may be disposed within the autosampler 104.

During operation of the flow cytometry system 100, various process liquids may be consumed by the autosampler 104 and/or the flow cytometer 102 and waste liquids from such processing must be collected. Such process liquids that may be supplied to the autosampler 104 and/or the flow cytometer 102 include, for example, rinse buffer solution, wash liquid and sheath liquid. Waste liquids may include process samples and sheath fluid after being subjected to flow cytometry analysis, as well as used rinse buffer solution and used wash liquid. One or more containers for providing these or other process liquids and/or containers for receiving waste liquids may be disposed in one or both of the autosampler 104 and the flow cytometer 102. However, it may be convenient to provide one or more liquid containers for such purpose external to the flow cytometer 102 and the autosampler 104, permitting significant flexibility in accommodating use of a combination of various flow cytometers and autosamplers not specifically designed and manufactured to interconnect and interface with each other, such as may be the case if they were designed and manufactured by a single manufacturer.

The system integration structure 106 includes a container rack 126 with a plurality of receptacles 128 configured to receive a corresponding plurality of process liquid containers that may provide a source of process liquid or a vessel to receive used process liquid, such as waste liquid, from operations involving the flow cytometer 102 and/or the autosampler 104. The flow cytometer system 100 as shown in FIG. 1 includes a plurality of process liquid containers 130a-d received in the receptacles 128 and with fluid conduits 132a-d fluidly connected with corresponding ones of the process liquid containers 130a-d. Each of the fluid conduits 132 is in fluid communication with either the flow cytometer 102 or the autosampler 104, or possibly with both. The receptacles 128 may be configured with a cross-section to correspond with a cross-section of process liquid containers to be received in the receptacles (e.g., corresponding circular cross-sections). One or even all of the receptacles 128 may have a different cross-section configuration from one or more other receptacles 128 to key with different corresponding exterior cross-sectional shapes of different process liquid containers 130.

In the particular implementation shown in the figures, the container rack 126 is formed as a unitary piece. In alternative implementations, the features of such a container rack 126 may be provided in a plurality of pieces that provide receptacles 128 to receive a sufficient number of process liquid containers 130 appropriately located in relation to the access opening feature 136. For example, one or more of all of the receptacles 128 may be provided in one rack piece, or in one assembly of multiple rack pieces, and one or more other ones of the receptacles 128 may be provided in one or more other rack pieces, or assemblies of multiple rack pieces. Such different rack pieces or assemblies need not be contiguous.

Each of the fluid conduits 132 is routed toward the flow cytometer 102 or the autosampler 104 through a routing channel that is within a first support member 134 of the system integration structure 106. The routing channel within the first support member 134 extends through the full length of the first support member 134 between the lower shelf 108 and the upper shelf 110. The fluid conduits 132 are routed into the routing channel within the first support member 134 through an access opening feature 136, which is shown in FIGS. 1 and 2, and may be in the form of one or a plurality of holes passing through a side wall of the first support member 134. As shown in FIG. 1, the access opening feature 136 may include holes that are sized to accommodate passage of only a single one of the fluid conduits 132 through each hole. The access opening feature 136 is at a vertically elevated position relative to the elevation of the receptacle 128, and relative to the tops of the process liquid containers 130 when received in the receptacles 128. This is the case whether a fluid conduit 132 will be routed upward through the routing channel in the first support member 134 toward the flow cytometer 102 or will be routed downward through the routing channel toward the autosampler 104. As seen in FIG. 4, holes 138 of the access opening feature 136 may be configured to receive a grommet (e.g., a rubber grommet) sized to snuggly fit around the fluid conduits 132 to help retain the fluid conduits 132 and prevent them from moving around over time or during operations to fill or remove liquid from the process liquid containers 130. The access opening feature 136 may include a number of the holes that is at least equal to the number of receptacles 128, or that may even be greater than the number of receptacles 128 to accommodate multiple fluid conduits 132 to a single process liquid container 130, for example to provide pressurized gas to a process liquid container 130 to provide pressurization to drive liquid out of the respective process liquid container 130 to the flow cytometer 102 or the autosampler 104, as the case may be. In some implementations, the container rack may include four of the receptacles 128 or may include a greater or smaller number of such receptacles 132 to provide locations for a greater or smaller number of process liquid containers 130. For some implementations, the access opening feature 136 may include at least six holes for passing the fluid conduits 132, with six to eight holes often being sufficient for accommodating four process liquid containers 130. The implementation of the system integration structure 106 shown in the figures includes seven such holes.

Although in the particular implementation shown in the figures the access opening feature 136 includes a plurality of holes, in alternative implementations, the access opening feature may include a single, larger opening through the wall of the first support member 134 through which all of the fluid conduits 132a-d may pass together. In other alternative implementations, the access opening feature 136 may include a plurality of openings through the side wall of the first support member 134 with multiple ones of the fluid conduits 132 passing through one or more of the openings together. And yet in other alternative implementations, holes of the access opening feature 136 may be arranged in a different configuration than the linear configuration shown in the figures. For example, such a configuration may include any geometric pattern for spacing the holes in a desired manner.

The routing channel through the first support member 134 extends upward from the access opening feature 136 and is open to an opening 140 through the upper shelf 110 and through which the fluid conduits 132 may be routed for fluid connection with the flow cytometer 102. The routing channel through the first support member 134 extends downward from the access opening feature and is open to a space 142 located below the lower shelf 108. Fluid conduits 132 may be routed through the space 142 to the side of the lower shelf 108 opposite the first support member 134 and may be routed through two routing holes 144 through the lower shelf 108 to permit fluid connection of the fluid conduits 132 with the autosampler 104. In some implementations, the lower shelf 108 could be eliminated from the system integration structure 106, and the autosampler 104 could be disposed, for example, directly on the surface, such as a surface of a table or work bench, on which the system integration structure 106 is supported. Including the lower shelf 108 is preferred to provide additional stability to the flow cytometer system 100 and to provide the space 142 below the lower shelf 108 for routing fluid conduits 132 to the autosampler 104.

As seen in FIG. 3, the first support member 134 includes an access piece 145, shown in the form of an access panel, located on the inside of the first support member 134 and which may be removed to permit access to the routing channel to facilitate easy threading of the fluid conduits 132 through the routing channel in the appropriate direction toward the flow cytometer 102 or the autosampler 104. In some implementations, a fluid conduit 132 may be branched within the routing channel within the first support member 134 into separate fluid conduit branches with one fluid conduit branch connecting with the flow cytometer 102 and another fluid conduit branch connecting with the autosampler 104. For example, one fluid conduit branch may receive waste liquid from the flow cytometer 102, while the other fluid conduit branch may receive waste liquid from the autosampler 104, and both such waste liquids may be directed to and received within a single process liquid container 130 through a single fluid conduit 132 to that process liquid container 130. As shown in FIG. 7, the flow cytometer 102 may include a single pass-through port 146 through which a bundle of all of the fluid conduits 132 directed to the flow cytometer 102 may be provided to the interior of the flow cytometer 102 to make the appropriate fluid connections within the flow cytometer 102.

The system integration structure 106 includes a second support member 148 disposed opposite the first support member 134. The first support member 134 and the second support member 148 together fully support the upper shelf 110 and the flow cytometer 102. The first support member 134 and the second support 148 member define a vertical separation distance between the lower shelf 108 and the upper shelf 110 to provide sufficient vertical space for receiving the autosampler 104 to be disposed between the lower shelf 108 and the upper shelf 110. The first support member 134 and the second support member 148 are spaced sufficiently far apart to permit at least a back portion of the autosampler 104 between the first support member 134 and the second support member 148. The routing holes 144 through the bottom shelf 108 are located in front of the second support member 148 to provide access for routing fluid conduits 132 to a side of the autosampler 104 opposite the container rack 126. The lower shelf 108 has a front edge 150 toward a front side of the system integration structure 106 and a back edge 152 toward a back side of the system integration structure 106. Likewise, the upper shelf 110 includes a front edge 154 toward the front side of the system integration structure 106 and a back edge 156 toward the back side of the system integration structure 106. The first support member 134 and the second support member 148 are disposed in the rear half of the system integration structure 106 to provide for easy access from the front and sides of the system integration structure 106 to the autosampler 104. The autosampler 104 has a front access in the form of the front door 122 that is easily accessible from the front of the system integration structure 106. The side access 124 is also easily accessible from the side of the system integration structure 106 without interference from the first support member 134, as the first support member 134 is not disposed opposite the side access 124. The system integration structure 106 is also open to the back to permit easy access to the back of the autosampler 104. If the autosampler 104 includes side access through the side of the autosampler 104 opposite the side access 124, the second support member is preferably not opposite such additional side access so that such additional side access is easily accessible from the side of the autosampler 104 adjacent the second support member 148.

The upper shelf 110 includes a number of features for accommodating the flow cytometer 102. The upper shelf 110 includes a plurality of registration recesses 158, shown in the form of circular recesses in the center of disks retained on the top surface of the upper shelf 110. Such disks may be, for example, in the form of metal washers attached to surrounding surfaces of the upper shelf 110. The registration recesses 158 are sized and located to correspond with a plurality of feet 160 of the flow cytometer 102. The feet 160 are retained in a fixed relation to the upper shelf 110 by the registration recesses 158 to prevent the flow cytometer 102 from moving laterally on the upper shelf 110 during use, which could for example damage the sample inlet 112 of the flow cytometer 102. In one enhancement, the feet 160 may be made of an elastomeric material to provide motion dampening (e.g., some level of vibration isolation) to the flow cytometer 102. Likewise, in another enhancement, feet 162 (shown in FIG. 1) on which the system integration structure 106 is supported may likewise be of an elastomeric material that provides additional motion dampening to the system integration structure 106 and consequently also to the flow cytometer 102. As will be appreciated, providing for vibration isolation to the flow cytometer 102 may be significantly beneficial in preventing vibrational or other motions from interfering with flow cytometry analysis.

The upper shelf 108 includes a perimeter liquid containment lip 156 that completely surrounds the perimeter of the flow cytometer 102 and provides for containment of liquid on the upper shelf 110 in the event that liquid should spill or otherwise collect on the upper shelf 110. The liquid containment lip 156 may have a height for fluid containment of at least 1 centimeter, at least 2 centimeters, at least 3 centimeters, at least 4 centimeters, at least 5 centimeters or more, and may in some implementations be not larger than 10 centimeters or even not larger than 5 centimeters in height, to provide significant fluid containment capacity while still providing for relatively easy access to the flow cytometer 102.

In some implementations, not shown in the figures, one or more of the process liquid containers 130 may have multiple fluid conduits 132 fluidly connected with the process liquid container 130. For example, in some implementations process liquid may be caused to flow from a process liquid container 130 to the flow cytometer 102 and/or to the autosampler 104 by pressurized gas (e.g., pressurized air, nitrogen or other gas) applied through one of the fluid conduits 132 to force flow of process liquid from the process liquid container 130 through another one of the fluid conduits 132 connected with the process liquid container 130. Such a gas fluid conduit 132 may be in fluid communication with a source of compressed gas to pressurize the process liquid container. In one enhancement, such a gas fluid conduit 132 to a process liquid container 130 may be fluidly connected with the source of compressed gas through the flow cytometer 102, which may control the delivery of pressurized gas through the gas fluid conduit 132 to the corresponding process liquid container 130. Such a gas fluid conduit 132 may be routed through the routing channel through the first support member 134 to a connection in the flow cytometer 102 for supply of compressed gas through the gas fluid conduit 132. As shown in FIG. 7, the flow cytometer 102 may include a gas line connector 164 which may be fluidly connected with a pressurized gas source, such as pressurized gas in a bottle or a compressed gas delivery system within a facility. Multiple ones of such process liquid containers 130 may each be connected with multiple such fluid conduits 132, with one providing pressurized gas to drive liquid flow from the process liquid container 130. One process liquid that may be contained within one of the process liquid containers 130 may be a sheath fluid, typically an aqueous liquid, that may be used in the flow cytometer 102 to hydrodynamically focus sample fluids for flow cytometry analysis by the flow cytometer 102. Flow of such a sheath fluid, for example, may be driven by pressurized gas delivered to a process liquid container 130 in such a manner.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible embodiments and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed variation may be combined in any combination with one or more of any other features of any other variation or variations, to the extent that the features are not necessarily technically compatible, and all such combinations are within the scope of the present invention. The description of a feature or features in a particular combination do not exclude the inclusion of an additional feature or features. Processing steps and sequencing are for illustration only, and such illustrations do not exclude inclusion of other steps or other sequencing of steps. Additional steps may be included between illustrated processing steps or before or after any illustrated processing step.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that something "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. A flow cytometer system, comprising:
  a flow cytometer with a sample inlet for receiving a sample fluid for flow cytometry analysis of the sample fluid for particles within the sample fluid;
  an autosampler in fluid communication with the sample inlet of the flow cytometer and operative to automatically provide a series of batches of sample fluid to the flow cytometer for flow cytometry analysis;
  a system integration structure, comprising:
    an upper shelf disposed above the autosampler and on which the flow cytometer is supported above the autosampler;
    a container rack comprising a plurality of container receptacles to receive a corresponding plurality of process liquid containers to provide a source of process liquid to and receive used process liquid from operations of the flow cytometer and autosampler; and
    a routing channel to route fluid conduits from process liquid containers toward the flow cytometer and the autosampler when the liquid containers are received in the container rack;
  at least one access opening into the routing channel to provide access for routing the fluid conduits from outside of the routing channel to inside the routing channel, wherein:
    the routing channel extends from the at least one access opening in an upward direction for routing of one or more of the fluid conduits to the flow cytometer located at a higher elevation than the at least one opening;

the routing channel extends from the at least one access opening in a downward direction for routing one or more of the fluid conduits to the autosampler; and the at least one access opening is located at a vertically elevated position relative to the receptacles of the container rack; and a plurality of the process liquid containers received within the receptacles of the container rack and the fluid conduits in fluid communication with the process liquid containers;

and wherein:

each said process fluid container is in fluid communication with the flow cytometer or the autosampler through a said fluid conduit routed through the routing channel; and at least two of the received process liquid containers are each in fluid communication with at least two said fluid conduits, wherein one of said fluid conduits to a said process liquid container provides liquid from the said process liquid container to the flow cytometer or the autosampler and another of said fluid conduits is in fluid communication through the flow cytometer with a source of compressed gas to provide compressed gas to the said process liquid container from the flow cytometer to pressurize the said process liquid container.

2. The flow cytometer system according to claim 1, comprising a support member supporting the upper shelf, wherein the routing channel passes through the support member, wherein the at least one access opening is through a side wall of the support member to provide access for routing the fluid conduits from outside of the support member to the routing channel in the support member.

* * * * *